United States Patent [19]

Marples et al.

[11] Patent Number: 4,681,876

[45] Date of Patent: Jul. 21, 1987

[54] ANTIFUNGAL UTILITY OF BILE ACIDS

[75] Inventors: Brian A. Marples, Loughborough; Reginald J. Stretton, Quorn, both of England

[73] Assignee: National Research Development Corporation, London, England

[21] Appl. No.: 755,016

[22] Filed: Jul. 15, 1985

[30] Foreign Application Priority Data

Jul. 13, 1984 [GB] United Kingdom ............... 8417895

[51] Int. Cl.$^4$ ......................... A61K 31/56; C07J 1/00
[52] U.S. Cl. ................................ 514/182; 260/397.1
[58] Field of Search ...................... 260/397.1; 424/45; 514/182

[56] References Cited

U.S. PATENT DOCUMENTS

| | | | |
|---|---|---|---|
| 4,164,573 | 8/1979 | Galinsky | 424/178 |
| 4,434,159 | 2/1984 | Sekine et al. | 424/178 |
| 4,440,688 | 4/1984 | Scolastico et al. | 260/397.1 |
| 4,579,730 | 4/1986 | Kidron et al. | |

FOREIGN PATENT DOCUMENTS

| | | | |
|---|---|---|---|
| 683192 | 11/1952 | United Kingdom | 260/397.1 |
| 848333 | 9/1960 | United Kingdom | 260/397.1 |
| 1430324 | 3/1976 | United Kingdom | 260/397.1 |
| 1563311 | 3/1980 | United Kingdom | 260/397.1 |
| 1601613 | 11/1981 | United Kingdom | 260/397.1 |
| 2116036A | 9/1983 | United Kingdom | 260/397.1 |

OTHER PUBLICATIONS

"Steroids" by Fieser et al., pages relied on.
M. E. Macintosh and R. H. Pritchard, Genet. Res. Camb. 4, 320–322 (1963).
S. De Nollin and M. Borgers, Antimicrobial Agents and Chemotherapy 7, 704–711 (1975).
Ziv et al., Life Sciences 29, 803–809 (1981).
Littman, M. L., "Growth of Pathogenic Fungi on a New Culture Medium", Technical Section, Dept. of Pathology & Bacteriology, Tulant Univ., New Orleans, Lousiana, pp. 409–420.
Haslewood, G. A. D. "Bile Salts" Methuen & Co. Ltd., London, p. 105, Appendix.
Wieland, H. et al., Zeitschrift fuer physiologische Chemie 214, 47–58 (1983), 47–58 with partial translation.
"The Merck Index", 10th Edition, Merck & Co., Inc. Rahway, N.J. USA, (1983) pp. 627 and 628, item 4254; and p. 994, item 6802.
"Kirk–Othmer Encyclopedia of Chemical Technology", 3rd Edition, John Wiley & Sons, New York (1979), vol., 5, p. 500.
"The Pharmacological Basis of Therapeutics" by L. S. Goodman and A. Gilman, 3rd ed., The MacMillan Company, New York 1965, pp. 1003 to 1007.
The Merck Index, 10th ed. 1983, entres 2183 and 8951.
"Oxford Textbook of Medicine", Ed. D. J. Weatherall et al., Oxford University Press 1983, vol. 1, Section 12-171.
G. D. Bell et al., The Lancet, Dec. 9, 1972, pp. 1213–1217.
R. G. Danzinger et al., The New England Journal of Medicine 296, 1–8 (1972).
S. Aonuma et al., Yakugaku Kenkyu 38, 381–392 (1967).
K. Saito, Odontology (Journal of Nippon Dental University) 6 (5), 650–671 (1979).
H. H. Gadebusch et al., The Journal of Infectious Diseases 134, 423–427 (1976).
P. B. Fisher et al., In vitro 12, 133–139 (1976).

*Primary Examiner*—Leonard Schenkman
*Assistant Examiner*—Joseph A. Lipovsky
*Attorney, Agent, or Firm*—Murray and Whisenhunt

[57] ABSTRACT

A valuable alternative antifungal antibiotic, for treatment especially of candidiasis, particularly vaginal candidiasis, is proposed. The antibiotic is a bile acid or simple derivative (salt or conjugate) thereof. Cholic, deoxycholic, chenodeoxycholic and lithocholic acid are preferred bile acids. The antibiotic is formulated for topical application. It can be used in association with an anti-inflammatory steroid for the treatment of fungal infections of the skin. It is also proposed to inhibit fungal growth in a variety of pharmaceutical compositions (containing some other active ingredient) by including in the composition, or coating a tablet, pill or capsule with, the bile acid component.

6 Claims, 6 Drawing Figures

ANTIFUNGAL UTILITY OF BILE ACIDS

BACKGROUND OF THE INVENTION

1. Field of the invention

This invention relates to a pharmaceutical composition for antifungal use, especially anti-Candida use (for treatment of the infection known as candidiasis).

2. Description of prior art

The antibiotics most commonly used for treatment of candidiasis, especially vaginal candidiasis are polyenes, especially nystatin. Such polyenes are not always effective if applied topically and their systemic administration is suspected of giving rise to kidney failure in some patients.

An antifungal cream and dusting powder based on miconazole is available under the Trade Mark "Daktarin" from Janssen Pharmaceutical Ltd. Since occasional irritation has been reported when using this product, it would be advantageous to have an alternative product for topical application.

Another imidazole, ketoconazole, has been used as a systemic fungicide, but recently there have been reports of hepatitis or liver damage occurring in some patients treated with ketoconazole, see Committee for Safety of Medicines Data Sheet, April 1983, and the article "New antifungal and antiviral chemotherapy" by J. C. M. Stewart et al., British Medical Journal, 286, 1802–1804 (1983).

There has therefore been a need to develop new antibiotics for the treatment of candidiasis.

Additional prior art is described below after the "Summary of the invention", without which its context would not be clear.

SUMMARY OF THE INVENTION

It has now been found, very surprisingly, that bile acids and their simple derivatives have anti-Candida activity.

An important feature of the invention consists in a pharmaceutical composition in a form suitable for topical application, comprising (1) a bile acid component in the form of at least one bile acid or a derivative thereof which is a conjugate thereof formed between the carboxylic acid of the bile acid and the $NH_2$ group of an amino acid having 3 to 6 chain atoms, inclusive of the amino and acid groups, or a salt of such an acid or conjugate, and (2) a pharmaceutically acceptable excipient for topical application.

The above feature of the invention can be formulated as the use of the bile acid component for the manufacture of a medicament for the therapeutic application of treating topical fungal infections, preferably candidiasis, and especially vaginal candidiasis.

The bile acid component is also useful for protecting any pharmaceutical composition against fungal growth. According to a second feature of the invention, therefore, there is provided a pharmaceutical composition in a solid or semi-solid form comprising at least the following three components: (1) an active ingredient in association with (2) a pharmaceutically acceptable excipient and (3) a bile acid component defined as above (compatible with the required purpose of the pharmaceutical composition, whether it is for topical application or some other route of administration). In this aspect of the invention the active ingredient is self-evidently not itself a bile acid component. That is, the bile acid component is additional to the active ingredient which can in principle be any conventional pharmaceutical material susceptible to fungal attack.

The bile acids referred to above are compounds of the general formula

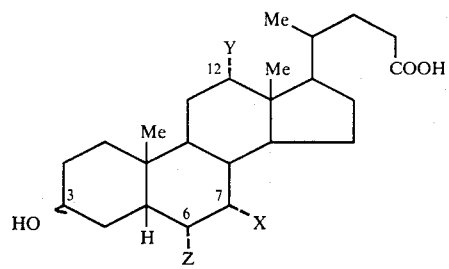

where Me represents a methyl group, X represents a hydrogen atom or a hydroxyl group (in the 7α-position), Y represents a hydrogen atom or hydroxyl group (in the 12α-position) and Z represents a hydrogen atom or hydroxyl group (in the 6α-position). These compounds are:

Cholic acid: 3α, 7α, 12α-trihydroxy-5β-cholan-24-oic acid

Deoxycholic acid: 3α, 12α-dihydroxy-5β-cholan-24-oic acid

Lithocholic acid: 3α-hydroxy-5β-cholan-24-oic acid

Chenodeoxycholic acid: 3α, 7α-dihydroxy-5β-cholan-24-oic acid

Hyodecholic acid 6α, 7α-dihydroxy-5β-cholan-24-oic acid

Hyodeoxycholic acid 6α-hydroxy-5β-cholan-24-oic acid

The bile acid salts can be any of those which are pharmaceutically acceptable, especially sodium, as the compound permits. The conjugates include those with glycine ($NH_2CH_2COOH$) and taurine ($NH_2CH_2CH_2SO_3H$) for example, and are amides formed between $NH_2$ group of the amino acid and the carboxylic acid group of the bile acid. Preferably the amino acid has 3 or 4 chain atoms.

Additional description of prior art

The bile acids are produced in various mammals, including man, and are excreted in large quantities. This origin is a prima facie indication that they are unlikely to be toxic to man.

Various bile acid derivatives have been administered intravenously or orally to increase the flow of bile, i.e. as choleretics. Dehydrocholic acid (3,7,12-trioxo-5β-cholan-24-oic acid) is the most active. Others are ox bile extract, cholic acid, sodium glycocholate and sodium taurocholate. See "The Pharmaceutical Basis of Therapeutics" by L. S. Goodman and A. Gilman, 3rd edition., The MacMillan Company, New York 1965 pages 1003 to 1007 and The Merck Index, 10th edition, 1983, entries 2183 and 8951.

Chenodeoxycholic and ursodeoxycholic acids have been administered orally for the prevention and dissolution of gallstones, see Oxford Textbook of Medicine, Ed. D. J. Weatherall, J. G. G. Ledlingham and D. A. Warrell, Oxford University Press, Vol. 1, Section 12-171 (1983), G. D. Bell et al., The Lancet Dec. 9, 1972, pages 1213–1217 and R. G. Danzinger et al., The New England Journal of Medicine, 286, 1-8, (1972).

It is known that amino acid-conjugated cholic acid has an inhibitory effect on the growth of the bacteria

*Bacillus subtilis* and *Saccharomyces cerevisiae* and *carlsbergensis*, see S. Aonuma et al., Yakugaku Kenkyu 38, 381–392 (1967). The compounds tested were however ineffective against *Escherichia coli* bacteria and against the fungus *Asperillus niger*.

The anti-Candida preparation Fungizone is administered intravenously and is sold in the form of 20 ml vials each containing amphotericin B together with 41 mg of sodium deoxycholate as a dispersant to "solubilize" the amphotericin and sodium phosphate buffer. Toxicity tests were carried out on Fungizone and separately on sodium deoxycholate by K. Saito, Odontology (Journal of Nippon Dental University) 6 (5), 650–671 (1979). The paper nowhere suggests that sodium deoxycholate has any fungicidal activity. Other papers relating to "Fungizone" are H. H. Gadebusth et al., The Journal of Infectious Diseases 134, 423–427 (1976) and Paul B. Fisher et al., In vitro, 12, 133–139 (1976).

M. E. Macintosh and R. H. Pritchard, Genet, Res. Camb. 4, 320–322 (1963) investigated the effect of the surface active agents sodium dodecyl sulphate and sodium deoxycholate on growth of *Aspergillus nidulans*, in the hope that they might promote growth. It was concluded that sodium deoxycholate had a growth-enhancing effect and the authors mention that after making this finding they learned that sodium deoxycholate was known to promote the growth of *Neurospora* and *Syncephalastrum*.

In the light of these prior disclosures, it was surprising to find by the present invention, that a bile acid or derivative thereof such as sodium deoxycholate, sodium cholate, or the like has at least a fungistatic effect on strains of Candida.

BRIEF DESCRIPTION OF THE DRAWINGS

In the Examples hereinafter reference is made to the accompanying drawings, in which.

DESCRIPTION OF THE PREFERRED EMBODIMENTS

Figure 1:
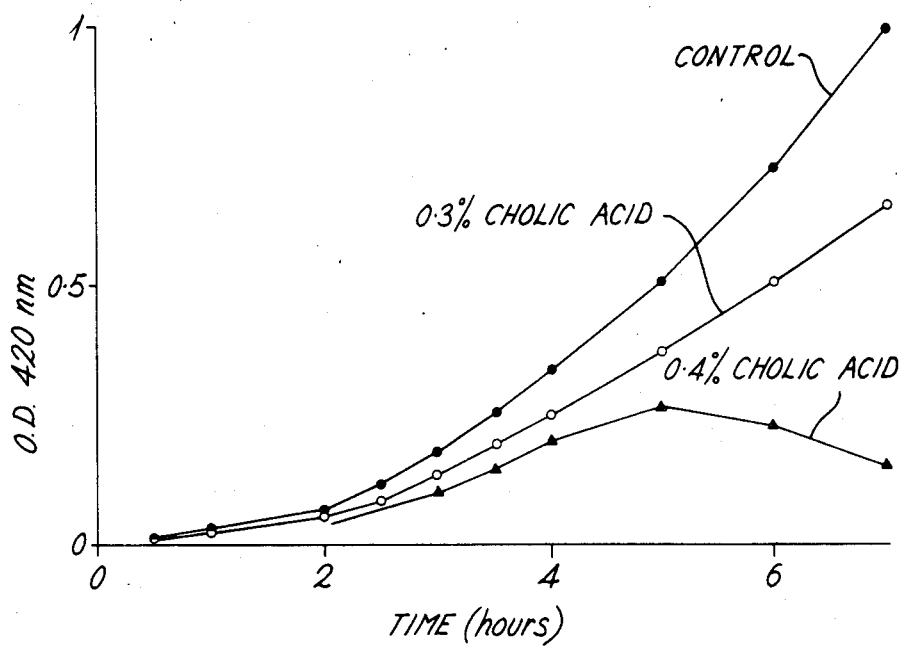
FIG. 1 is a plot showing growth of *Candida albicans* in the presence of various amounts of sodium cholate.

The bile acid component can be formulated in any conventional way suitable for topical application, for example as a capsule, suppository or pessary for intracavital application (to the vagina, urethra or rectum) or a gel, ointment, cream or the like, dusting powder or aerosol spray. A suppository or pessary may contain theobroma oil, glycerinated gelatin or polyethylene glycol, for example, as a carrier which melts at body temperature or dissolves in body fluids. The bile acid component can be formulated as an ointment or cream with an oleaginous or waxy binder. An aqueous phase may be present, to provide a cream. Other forms of formulation include gelatin capsules containing the ingredient in a liquid diluent, mixtures with talc or the like to provide dusting powder and aerosol bombs which comprise the ingredient and an inert propellant.

A preferred formulation is an ointment or cream containing say, from 1 to 5 percent by weight of the bile acid component depending on its effectiveness.

Tablets for oral administration of cholic acid, containing merely a choleretic or gallstone-dissolving amount of a bile acid component for such a use, are not within the scope of the invention. Other tablets and pills, for intravaginal use for example, are within the scope of the invention. They may contain conventional inert excipients for the intended purpose. Such pessaries can be formulated as controlled release compositions using as excipient a polymeric carrier comprising residues which are cross-linked through urethane groups and which comprise polyethylene oxide, as described in UK Patent Specification No. 2047093A (National Research Development Corporation).

A particularly preferred aspect of the invention comprises the bile acid component in association with an anti-inflammatory agent, especially of the steroidal type, most especially a corticosteroid, e.g. betamethasone, fluocinolone acetonide, beclomethasone dipropionate, hydrocortisone, cortisone or cortisol. These compositions are useful for the treatment of fungal infections of the skin.

A reasonable prediction from the information available is that the invention would be useful in treating the same kinds of topical fungal infections as miconazole.

It is contemplated that the bile acids and derivatives could also be formulated as an aerosol for application to the orapharynx or upper respiratory tract, orally or intranasally.

Referring now to the second feature of the invention, namely the use of the bile acids and derivatives to inhibit fungal attack on pharmaceutical preparations such as tablets, capsules, creams, ointments pessaries and suppositories, tablets can be coated with the bile acid component or any of the preparations can contain a small proportion of bile acid component effective to confer on it resistance to fungal attack. This would ordinarily be a subtherapeutic amount, especially a subcholeretic amount. In general the amount of bile acid or derivative per dosage unit should be from 1–10 mg, especially about 5 mg. In this way it would be possible in particular to protect tablets made by wet granulation processes where fungal attack is particularly serious.

The following Examples illustrate the invention. Proportions expressed as weight/volume are metric, i.e. g/100 ml.

EXAMPLE 1

The strains of *Candida albicans* used were A39 (a clinical isolate provided by Boots PLC, Nottingham, England) and CMI 45348 (available as an ordinary scientific deposit from the Commonwealth Mycological Institute, Ferry Lane, Kew, Surrey TW9 3AF, England).

Starter cultures were made by growing the *Candida albicans* in an aqueous medium in shake culture at 140 rpm in an orbital incubator for 18 hours at 30° C. The medium used consisted of Tris, 1.2 g; NaCl, 0.1 g; Ammonium tartrate, 5.0 g; Ammonium nitrate, 1.0 g; $KH_2PO_4$, 1.0 g; $MgSO_4.7H_2O$, 0.5 g; $CaCl_2$, 0.1 g; glucose, 100 g; and biotin $1 \times 10^{-5}$ g, all per liter, to which was added 1.0 ml per liter of a mineral salts solution which contained $H_3BO_3$, 6 mg; $(NH_4)_6 MoO_{24}.4H_2O$, 26 mg; $FeCl_3.6H_2O$, 100 mg; $CuSO_45H_2O$, 40 mg; $MnCl_2.4H_2O$, 8 mg; and $ZnCl_2$, 200 mg, all per 100 ml of mineral salts solution. 5 ml aliquots of this starter culture were then transferred to 100 ml volumes of fresh medium of the same composition, to which aqueous sodium cholate solution has been added to give the required test concentration. In a control experiment, no sodium cholate was added. These cultures were incubated at 140 rpm at 30° C. and the optical density measured at 420 nm at definite time intervals.

The concentrations of the sodium salt of cholic acid (reckoned as the salt) used and the responses were as follows:

| Control | no response |
|---|---|
| 0.001% w/v | no response |
| 0.01% w/v | no response |
| 0.1% w/v | no significant response |
| 0.2% w/v | |
| 0.3% w/v | response as shown in FIG. 1 of the drawings. |
| 0.4% w/v | |
| 0.5% w/v | no growth after 3 hours |
| 1.0% w/v | no growth after 3 hours |

Figure 2:
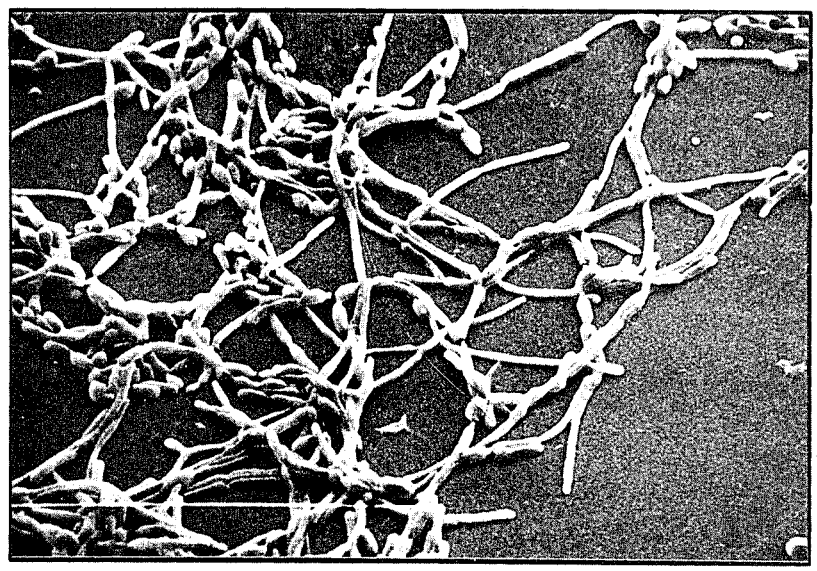
FIG. 2 is a photograph of untreated cells of *Candida albicans;*.
Figure 3:
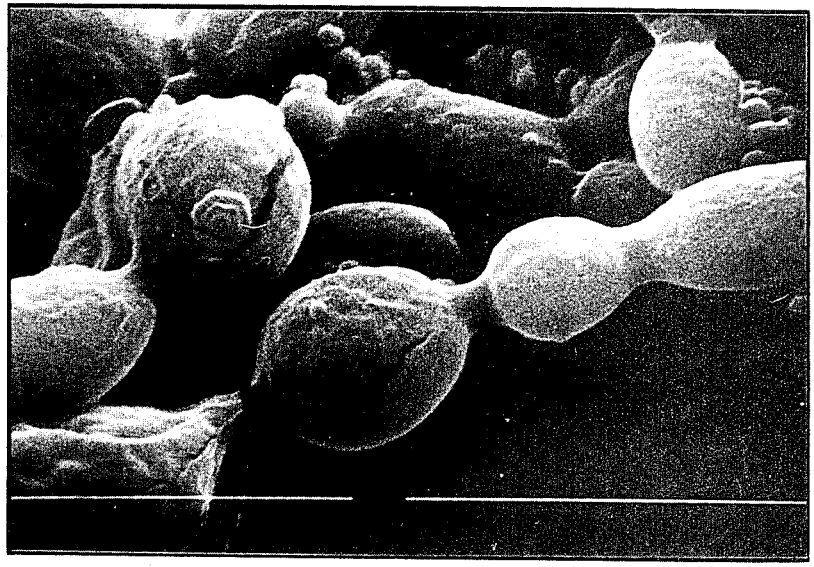
FIGS. 3 to 6 are photographs of cells of *Candida albicans* treated with various amounts of various bile acid components, namely sodium salts of cholic, chenodeoxycholic, lithocholic or deoxycholic acids.

FIG. 2 of the drawings shows normal control cells of *Candida albicans* (A39 strain) and FIG. 3 cells of the same strain grown in the presence of 0.4% w/v sodium cholate for 6 hours at 30° C. The principal differences between the cells of FIG. 3 and normal cells of *Candida albicans* are (a) that in FIG. 3 the lemon-shaped yeast-form cells are not dividing properly but are joined together by a relatively thick "neck" portion and (b) that in FIG. 3 the cell walls are cracked (whereas in normal Candida cells they are not). The FIG. 3 cellular morphology is similar to that observed by S. De Nollin and M. Borgers, Antimicrobial Agents and Chemotherapy, 7, 704–711 (1975), in *Candida albicans* treated with the antifungal agent miconazole, see especially FIG. 2 thereof.

EXAMPLE 2

The procedure of Example 1 was repeated using sodium salts of chenodeoxycholic acid, lithocholic acid and deoxycholic acid. All these salts are less soluble in water than sodium cholate. Because of the solubility problem, meaningful quantitative data at different concentrations of additive could not be obtained. Nevertheless, the experiments showed that each of these salts affected the cellular structure of the organism in a broadly similar way to the necking effect seen in FIG. 3. Since this effect was also observed in miconazole treatment, it can reasonably be concluded that these other bile acid salts also have an anti-Candida effect.

Figure 4:
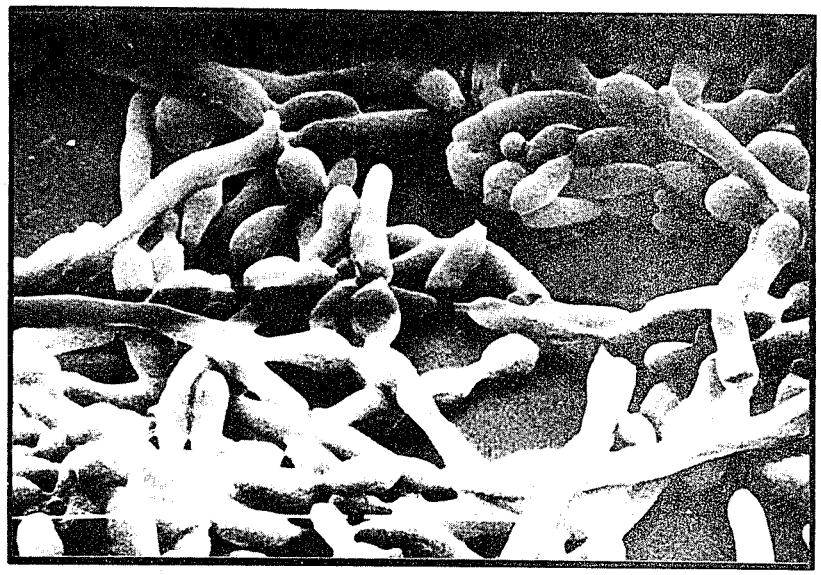
Figure 5:
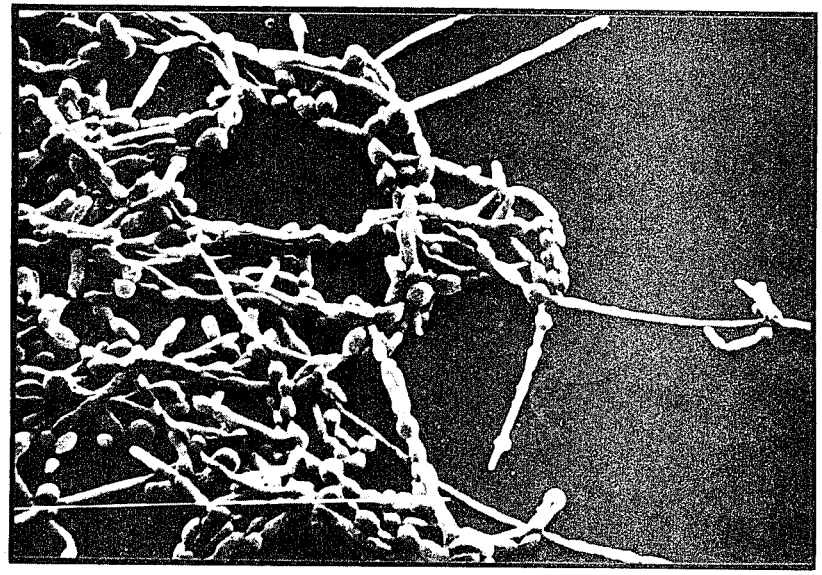
Figure 6:
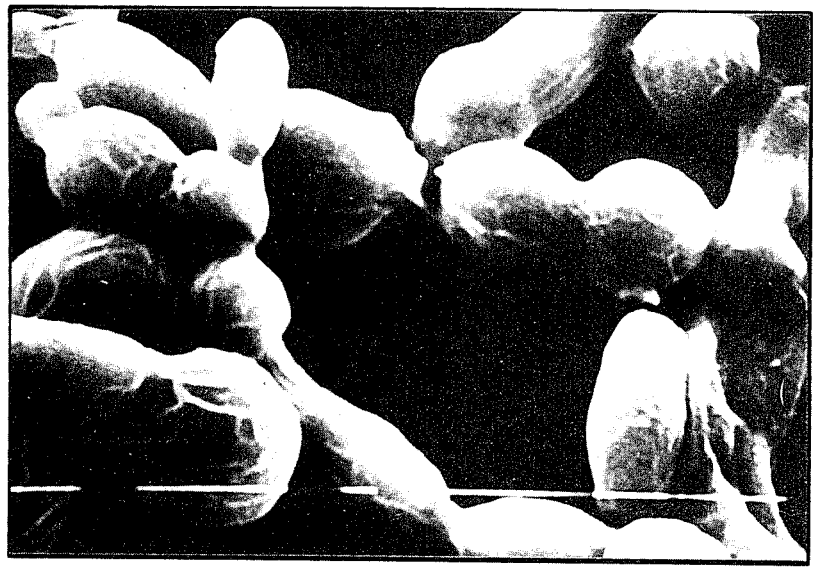

In more detail, the chenodeoxycholate treatment (1% w/v, sodium salt) caused the yeast cells to become incompletely separated after 6 hours growth at 30° C. and the amount of the elongated mycelial structure to increase, see FIG. 4. The necking effect is clearly visible. A lithocholate treatment (1% w/v, sodium salt) after 6 hours growth at 30° C. (FIG. 5) showed similar effects. When deoxycholate 0.05% w/v, sodium salt) was used instead, cell elongation, "necking", and incomplete separation were again observed (FIG. 6).

EXAMPLE 3

The effectiveness of various bile acids and derivatives of the invention to inhibit *Candida albicans* A39 on agar was demonstrated in spread and seeded plate tests. The plates had a diameter of 9 cm. In both tests a culture of $10^7$–$10^8$ cells/ml of the Candida organism was used. In the seeded plate test 1 ml of the culture was dispersed in agar to a total volume of 20 ml and the agar allowed to solidify. In the spread plate test 0.1 ml of the culture was spread on the surface of the solidified agar. 1% w/v solutions of the bile acids and derivatives were made in distilled water of if necessary in ethanol and sterilised by membrane filtration. Sterile 5 mm discs (Whatman AA) were dipped in these solutions and allowed to dry in sterile petri dishes. They were then placed on the surfaces of the plates to provide approximately 0.2 mg of bile acid or derivative per disc. The plates were then incubated for 24 hours at 30° C. The zones of inhibition, represented by cleared areas were then recorded. In nearly all cases they extended beyond the area of the disc, the *Candida albicans* having grown outwardly from the original 5 mm diameter area during the incubation and the bile acid or derivative being sufficiently potent an agent to inhibit it.

The results are shown in the Table below. It will be seen that most of the bile acids or derivatives gave good inhibition in both tests. Although two of them were effective only in the seeded plate test their performance in that test does indicate some anti-Candida activity.

TABLE
Zones of inhibition of growth of *Candida albicans* by bile acid

| Compound number | Compound | Zone of inhibition (cm) | |
|---|---|---|---|
| | | Spread plate | Seeded plate |
| 19 | Sodium cholate | 0.51 | 1.2 |
| 20 | Sodium deoxycholate | 0.73 | 0.81 |
| 21 | Chenodeoxycholic acid | 0.63 | 1.38 |
| 22 | Hyocholic acid | 0.69 | 0.55 |
| 23 | Hyodeoxycholic acid | 0.66 | 0.85 |
| 24 | Sodium lithocholate | 0 | 0.55 |
| 25 | Sodium glycocholate | 0 | 0.64 |
| 26 | Sodium glycodeoxycholate | 0.62 | 1.16 |

We claim:

1. A method of combatting a fungal infection in a human patient which comprises applying topically to the site of the infection in the patient at least one bile acid of the general formula

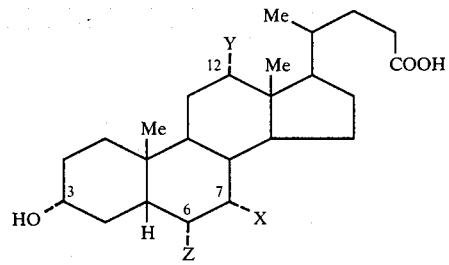

wherein Me represents a methyl group and each of X, Y and Z independently represents a hydrogen atom or a hydroxyl group or a derivative thereof which is a conjugate formed between the COOH group shown and the $NH_2$ group of an amino acid having 3 to 6 chain atoms, inclusive of the amino and acid groups, or a salt pharmaceutically acceptable of such an acid or conjugate.

2. A method according to claim 1 wherein the fungal infection is a candidiasis infection.

3. A method according to claim 1 wherein chenodeoxycholic acid or a pharmaceutically acceptable salt thereof is applied.

4. A method according to claim 3 wherein chenodeoxycholic acid or a said salt thereof is applied to the vagina.

5. A method according to claim 1 wherein deoxycholic acid or a pharmaceutically acceptable salt thereof is applied.

6. A method according to claim 5 wherein deoxycholic acid or a said salt thereof is applied to the vagina.

* * * * *